US012670566B2

(12) United States Patent
Auvray et al.

(10) Patent No.: US 12,670,566 B2
(45) Date of Patent: Jun. 30, 2026

(54) ENHANCING ANGIOGRAMS

(71) Applicant: KONINKLIJKE PHILIPS N.V., Eindhoven (NL)

(72) Inventors: Vincent Maurice André Auvray, Meudon (FR); Alexandre Jean Michel Popoff, Paris (FR); Raoul Florent, Ville d'Avray (FR)

(73) Assignee: Koninklijke Philips N.V., Eindhoven (NL)

( * ) Notice: Subject to any disclaimer, the term of this patent is extended or adjusted under 35 U.S.C. 154(b) by 214 days.

(21) Appl. No.: 18/698,515

(22) PCT Filed: Sep. 29, 2022

(86) PCT No.: PCT/EP2022/077093
§ 371 (c)(1),
(2) Date: Apr. 4, 2024

(87) PCT Pub. No.: WO2023/057296
PCT Pub. Date: Apr. 13, 2023

(65) Prior Publication Data
US 2024/0404031 A1 Dec. 5, 2024

(30) Foreign Application Priority Data
Oct. 6, 2021 (EP) .................................... 21290063

(51) Int. Cl.
*G06T 5/94* (2024.01)
*A61B 6/50* (2024.01)
(Continued)

(52) U.S. Cl.
CPC ................ *G06T 5/94* (2024.01); *A61B 6/504* (2013.01); *G06T 5/20* (2013.01); *G06T 5/50* (2013.01);
(Continued)

(58) Field of Classification Search
CPC .... G06T 5/94; G06T 5/20; G06T 5/50; G06T 5/60; G06T 2207/10116;
(Continued)

(56) References Cited

U.S. PATENT DOCUMENTS 9,805,465 B2   10/2017   Kyriakou
10,524,755 B2   1/2020   Kowarschik et al.
(Continued)

FOREIGN PATENT DOCUMENTS

KR        20080070353 A      7/2008

OTHER PUBLICATIONS

Silva et al., "Encoder-Decoder Architectures for Clinically Relevant Coronary Artery Segmentation", arXiv:2106.11447v1 [eess.IV] Jun. 21, 2021, pp. 1-17.
(Continued)

*Primary Examiner* — Kiho Kim

(57) ABSTRACT

The present invention relates to image processing of angiograms. A device for enhancing angiograms is provided. The device comprises a data input, a data processor, and an output interface. The data input provides at least one angiographic image showing a vascular structure of interest comprising a plurality of vessel branches. The data processor is configured to determine at least one branch of interest from the angiographic image, to segment the angiographic image for identifying possible branches of the vascular structure, to select branches based on the identified possible branches and the determined branch of interest, to estimate attenuation values of the selected branches, and to subtract at least a predetermined part of the estimated attenuation values from the angiographic image to generate a corrected angiogram. The output interface is configured to provide the corrected angiogram.

20 Claims, 5 Drawing Sheets

(51) Int. Cl.
| | |
|---|---|
| *G06T 5/20* | (2006.01) |
| *G06T 5/50* | (2006.01) |
| *G06T 5/60* | (2024.01) |
| *G06V 10/25* | (2022.01) |
| *G06V 10/26* | (2022.01) |
| *G06V 10/82* | (2022.01) |

(52) U.S. Cl.
CPC ............... *G06T 5/60* (2024.01); *G06V 10/25* (2022.01); *G06V 10/26* (2022.01); *G06V 10/82* (2022.01); *G06T 2207/10116* (2013.01); *G06T 2207/20084* (2013.01); *G06T 2207/20224* (2013.01); *G06T 2207/30101* (2013.01); *G06T 2207/30172* (2013.01); *G06V 2201/03* (2022.01)

(58) Field of Classification Search
CPC . G06T 2207/20084; G06T 2207/20224; G06T 2207/30101; G06T 2207/30172; A61B 6/504; A61B 6/5217; G06V 10/25; G06V 10/26; G06V 10/82; G06V 2201/03
See application file for complete search history.

(56) References Cited

U.S. PATENT DOCUMENTS

| | | | |
|---|---|---|---|
| 2013/0322724 A1 | 12/2013 | Florent et al. | |
| 2014/0029821 A1* | 1/2014 | Lee ...................... | G06T 7/0012 |
| | | | 382/131 |
| 2019/0336096 A1 | 11/2019 | Itu et al. | |
| 2019/0365336 A1* | 12/2019 | Wagner .................... | G06T 5/94 |
| 2020/0337773 A1 | 10/2020 | Rawlinson et al. | |
| 2021/0104040 A1 | 4/2021 | Nett | |

OTHER PUBLICATIONS

Ko et al., "A Fully Automated Identification of Coronary Borders from the Tree Structure of Coronary Angiograms", Elsevier, International Journal of Biomedical Computing 39, (1995), pp. 195-208.

Kern et al., "Angiographic projections made simple: an easy guide to understanding oblique views", CathLab digest, vol. 19, issue 8, Aug. 2011.

Xian et al., "Main Coronary Vessel Segmentation Using Deep Learning in Smart Medical Mathematical Problems in Engineering", vol. 2020, pp. 1-9, 2020.

Yang et al., "Deep learning segmentation of major vessels in X-ray coronary angiography", Scientific Reports, vol. 9 Issue 1, p. 16897, 2019.

Zhao et al., "Semantic segmentation to extract coronary arteries in fluoroscopic angiograms", medrxiv, Oct. 11, 2021.

Di Mario et al., "Coronary Angiography in the Angioplasty Era: Projections with a Meaning", Heart 2005;91, pp. 968-976.

International Search report and Written Opinion of PCT/EP2022/077093, dated Feb. 6, 2023.

* cited by examiner

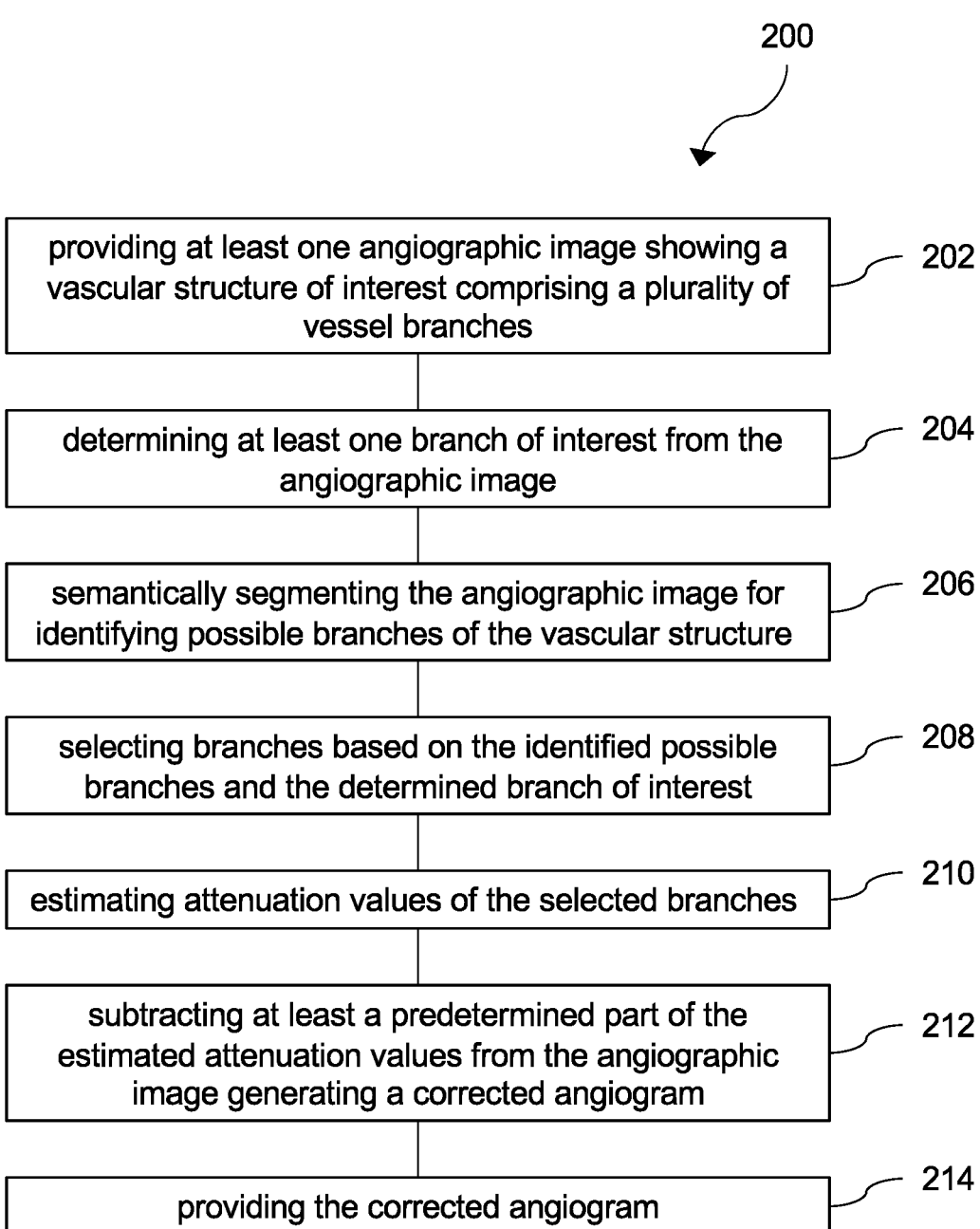

200 providing at least one angiographic image showing a vascular structure of interest comprising a plurality of vessel branches    202 determining at least one branch of interest from the angiographic image    204 semantically segmenting the angiographic image for identifying possible branches of the vascular structure    206 selecting branches based on the identified possible branches and the determined branch of interest    208 estimating attenuation values of the selected branches    210 subtracting at least a predetermined part of the estimated attenuation values from the angiographic image generating a corrected angiogram    212 providing the corrected angiogram    214

| Table 2 | Angiographic projections and optimal visualisation of left and right coronary artery segments | | | | | | | |
|---|---|---|---|---|---|---|---|---|
| Coronary artery segment | LAO 40 - 50°, caudal 25 - 45° (spider) | AP / RAO 5 - 15°, caudal 30° | RAO 30 - 45°, caudal 30 - 40° | AP / RAO 5 - 10°, cranial 35 - 45° | AP / RAO 30 - 45°, cranial 25 - 35° | Lateral ± caudocranial 10 - 30° | LAO 45 - 60° | RAO 30 - 45° |
| LM ostium | ++ | + | + | +++ | +++ | - | - | - |
| LM bifurcation | +++ | +++ | ++ | - | - | - | - | - |
| LAD proximal | ++ | ++ | ++ | ++ | ++ | + | - | - |
| LAD mid | - | + | + | +++ | ++ | +++ | - | - |
| LAD distal | + | + | +++ | + | - | +++ | - | ++ |
| LAD / diagonal | ++ | + | - | ++ | ++ | - | - | - |
| LCX proximal | + | +++ | +++ | - | - | + | - | - |
| LCX distal | + | + | ++ | - | ++ | + | ++ | - |
| OM bifurcation | ++ | +++ | ++ | + | ++ | - | + | - |
| RCA proximal | - | - | - | + | + | - | ++ | ++ |
| RCA mid | - | - | - | ++ | ++ | ++ | ++ | - |
| RCX distal / crux | - | - | - | ++ | ++ | - | ++ | - |
| PDA | - | - | - | ++ | ++ | + | + | + |
| PLV | + | - | - | - | - | + | + | - |
| LIMA anastomosis | + | - | - | - | - | +++ | - | - |

- View not recommended; + occasionally useful; ++ very useful; +++ idea; view.

AP, anteroposterion; LAD, left anterior descending; LAO, left anterior oblique; LCX, left circumflex; LIMA, left internal mammary; OM, obtuse marginal; PDA, posterior descending artery; PLV, posterior ventricular; RAO, right anterior oblique; RCA right coronary artery.

FIG. 4

ENHANCING ANGIOGRAMS

CROSS-REFERENCE TO PRIOR APPLICATIONS

This application is the U.S. National Phase application under 35 U.S.C. § 371 of International Application No. PCT/EP2022/077093, filed on Sep. 29, 2022, which claims the benefit of European Patent Application No. 21290063.3, filed on Oct. 6, 2021. These applications are hereby incorporated by reference herein.

FIELD OF THE INVENTION

The present invention relates to a device for enhancing angiograms, to a medical imaging system for assessment of vascular structures and to a method for enhancing angiograms.

BACKGROUND OF THE INVENTION

Vascular structures are three-dimensionally extending structures that can have spatially crossing branches. In particular the coronary artery tree presents a complex 3D structure, that a clinician needs to assess from a series of 2D projections, e.g. 2D X-ray images like fluoroscopic images. For visualizing the vessels, contrast agents can be used. For example, angiographic images are used to assess the vascular structure. The visibility of important vessel segments is frequently impaired by overlapping vessels, creating a clutter that makes a clear diagnosis tedious. As an example, the clinician may select specific views, e.g. certain C-arm angulations, to observe specific important vessel branches, e.g. proximal LAD, mid circumflex, etc. Those reference views, e.g. LAO caudal, RAO cranial, are preferred, because they present the vessel segment of interest with minimal foreshortening, and hopefully with minimal clutter. However, it has been shown that there are cases where the stenosed segment of interest can be observed at some time instants in a sequence of images, but overlapped at others. This makes the analysis more tedious, since it keeps being shown and hidden. Furthermore, in other situations, the segment of interest may be constantly overlapped.

SUMMARY OF THE INVENTION

There may thus be a need to provide improved angiograms.

The object of the present invention is solved by the subject-matter of the independent claims: further embodiments are incorporated in the dependent claims. It should be noted that the following described aspects of the invention apply also for the device for enhancing angiograms, for the medical imaging system for assessment of vascular structures and for the method for enhancing angiograms.

According to the present invention, a device for enhancing angiograms is provided. The device comprises a data input, a data processor and an output interface. The data input is configured to provide at least one angiographic image showing a vascular structure of interest comprising a plurality of vessel branches. The data processor is configured to determine at least one branch of interest from the angiographic image. The data processor is also configured to segment the angiographic image for identifying possible branches of the vascular structure. The data processor is further configured to select branches based on the identified possible branches and the determined branch of interest. The data processor is furthermore configured to estimate attenuation values of the selected branches. The data processor is also configured to subtract at least a predetermined part of the estimated attenuation values from the angiographic image to generate a corrected angiogram. The output interface is configured to provide the corrected angiogram.

As an effect, an angiogram is provided less cluttered and easy to read.

According to an example, the data processor is configured to select branches not of interest based on the identified possible branches and the determined, i.e. identified, branch of interest. The data processor is also configured to estimate attenuation values of the selected branches not of interest.

According to an example, for the subtraction, in a first option, the data processor is configured to subtract the complete estimated attenuation values of the branches not of interest from the angiographic image for the generation of the corrected angiogram. In a second option, the data processor is configured to subtract a predetermined part of the respective estimated attenuation values from the angiographic image for the generation of the corrected angiogram.

According to an example, for the segmentation of the angiographic image for identifying possible branches of the vascular structure, the data input is configured to provide geometric image acquisition parameters comprising at least one of the group of direction and angulation. The data processor is configured to, based on the geometric image acquisition parameters, select to be expected segments from a lookup table identifying possible segments that can be expected for certain geometric image acquisition parameters.

According to an example, the vascular structure of interest is the coronary artery tree. The lookup table is based on established guidelines listing angiographic projections and optimal visualization of coronary artery segments.

According to an example, for the estimation of the attenuation values of the selected branches not of interest, the data processor is configured to assume cylindrically shaped cross-sections for the branches.

According to an example, a display is provided configured to display the corrected angiogram.

According to the present invention, also a medical imaging system for assessment of vascular structures is provided. The system comprises an X-ray imaging device with an X-ray source and an X-ray detector and a device for enhancing angiograms according to one of the preceding examples. The X-ray imaging device is configured to provide the at least one angiographic image.

According to the present invention, also a method for enhancing angiograms is provided. The method comprising the following steps:

providing at least one angiographic image showing a vascular structure of interest comprising a plurality of vessel branches;

determining at least one branch of interest from the angiographic image;

semantically segmenting the angiographic image for identifying possible branches of the vascular structure;

selecting branches based on the identified possible branches and the determined branch of interest;

estimating attenuation values of the selected branches;

subtracting at least a predetermined part of the estimated attenuation values from the angiographic image generating a corrected angiogram; and providing the corrected angiogram.

According to an aspect, the identification of the segments of interest on the considered angiogram is provided plus a semantic segmentation of the coronary tree in its different branches. Further, a local model of the attenuation of each branch is computed, e.g. based on the assumption that the branch is locally tubular. For every branch that is not of interest from the considered view, a local model of its attenuation is computed, and subtracted from the original angiogram. This results in that mainly or even only the contrast agent present in the segment of interest will remain visible in the processed sequence.

In the first segmenting step, also referred to as segmentation of the segment of interest, the goal is to segment the pixels belonging to the branch(es) that belong to one of the vessel of interest (from the considered view). This can be achieved by Deep Learning. A network, typically a UNet, is trained based on numerous angiographic images that are associated a target segmentation of the vessels of interest, which may be labelled by experts. At inference, when provided a new angiographic image, the network outputs a proposed segmentation of the vessels of interest.

In the second segmenting step, also referred to as semantic segmentation into the different branches, the goal is to segment the pixels belonging to the vasculature, and to cluster them into different branches that can potentially overlap. One possible approach is to determine segmentation maps for the different anatomical branches: LAD, circumflex, first diagonal, etc. From the angiographic image, the algorithm will generate n segmentation maps, one for each (known) anatomical branch. This can also be implemented by Deep Learning. Once experts have segmented a large amount of images into their different anatomical branches, a network, typically also a UNet, can train on it, and is then able to perform the inference on new data.

The step of estimating attenuation values can also be referred to as segmented branch attenuation estimation. From the segmentation of one branch, it is of advantage to get the corresponding contrast attenuation on the original image, i.e. the grey-value shifts caused by the injection of that branch. Basically, the goal is to transform a binary segmentation into the vessel grey-values.

The semantic segmentation (the second step) can be can leveraged, and it is rather provided to only determine which branch of it is of interest, for instance by using the guidelines to build a look-up table.

As an example, this is performed by modelling the vessel as locally cylindrical. Hence, the vessel is considered as a cylinder of slowly varying radius and attenuation along its centerline. This local radius is known from the segmentation. Leveraging this model, a local attenuation can be estimated associated to each positions along the vessel centerline. The grey-value profile orthogonal to the centerline has a distinctive signature that derives from the cylinder model. By observing it, it is possible to estimate the local height of the signature profile, which in turns directly translates into a local attenuation.

Since the background under the vessel is not perfectly homogeneous (even locally), in an example, the observed profile is pre-processed, e.g. low pass filtering, bias correction and the like. In order to be robust to local overlaps to other objects (including vessels), in an example, some postprocessing of the estimated attenuations is performed along the centerline, like sliding median filtering.

The original image is processed for the determination of the segment of interest in order to determine which vessel segments need to be preserved. In parallel, it is processed semantic segmentation in order to determine a list of segmentations of the vessels present in the image. Then, the vessels that should not be preserved are considered one by one. Their local attenuation is estimated using the segmented branch attenuation estimation. The corresponding grey-values are reconstructed based on this model, and subtracted from the original image. Once that step has been performed, the considered vessel should visually disappear or at least appear rather weak and thus less distracting.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 3 shows basic steps of an example of a method for enhancing angiograms.

FIG. 4 shows an example of a table of related artery segments for certain viewing geometry.

DETAILED DESCRIPTION OF EMBODIMENTS

Figure 1:
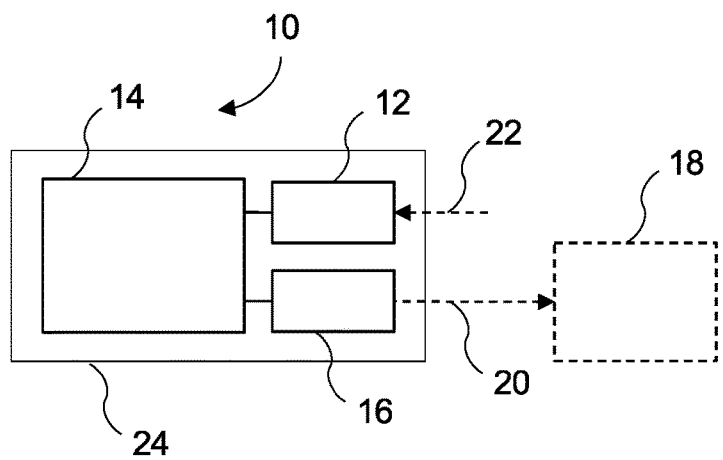
FIG. 1 schematically shows an example of a device for enhancing angiograms.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

FIG. 1 schematically shows an example of a device 10 for enhancing angiograms. The device 10 comprises a data input 12, a data processor 14 and an output interface 16. The data input 12 is configured to provide at least one angiographic image showing a vascular structure of interest comprising a plurality of vessel branches. The data processor 14 is configured to determine at least one branch of interest from the angiographic image. The data processor 14 is configured to segment the angiographic image for identifying possible branches of the vascular structure. The data processor 14 is configured to select branches based on the identified possible branches and the determined branch of interest. The data processor 14 is configured to estimate attenuation values of the selected branches. The data processor 14 is configured to subtract at least a predetermined part of the estimated attenuation values from the angiographic image to generate a corrected angiogram. The output interface 16 is configured to provide the corrected angiogram.

In an option, one segmentation is provided: the semantic segmentation. The determination of which branches are of interest can be provided, e.g., based on or from the look-up table, e.g. without looking at the image.

In another option, two different segmentations are provided: the segmentation of the branch of interest, and semantic segmentation into all the different anatomical branches.

In an example, for the determination of the at least one branch of interest, the data processor 14 is configured to segment the angiographic image for identifying at least one branch of interest. The data processor 14 is further configured to select branches based on the identified possible branches and the identified branch of interest.

The data input 12 can also be referred to as data input module. The data processor 14 can also be referred to as data processing module. The output interface 16 can also be referred to as output interface module.

The data input 12 can also be referred to as data supply, as image supply, as image data supply, as segmentation input, as input unit or simply as input. In an example, the data input 12 is data-connectable to an imaging source arrangement like a CT imaging system or MR imaging system providing the 2D image data of the subject which is used for the segmentations. In an example, the image data input is data-connectable to a data storage having stored the 2D image data.

The data processor 14 can also be referred to as data processing arrangement, as processor unit or as processor. In an example, the data processor 14 is data-connected to the image data input 12 and the output interface 16. In an example, the data processor 14 is provided as segmenting engine that determines, e.g. by segmentation, the angiographic image for determining, i.e. identifying at least one branch of interest and that segments the angiographic image for identifying possible branches of the vascular structure.

The output interface 16 can also be referred to as output or output unit. In an example, the output interface 16 is data-connectable to a display arrangement or display device. In another example, the output interface 16 is data-connected to a display.

As an option, depicted in hashed lines in FIG. 1, a display 18 is provided configured to display the corrected angiogram. A first hashed arrow 20 indicates the data transfer to the display 18. A second hashed arrow 22 indicates the data input. A frame 24 indicates an option providing input, processor and output in a common housing. In another example, these are provided as separate components.

Figure 2:
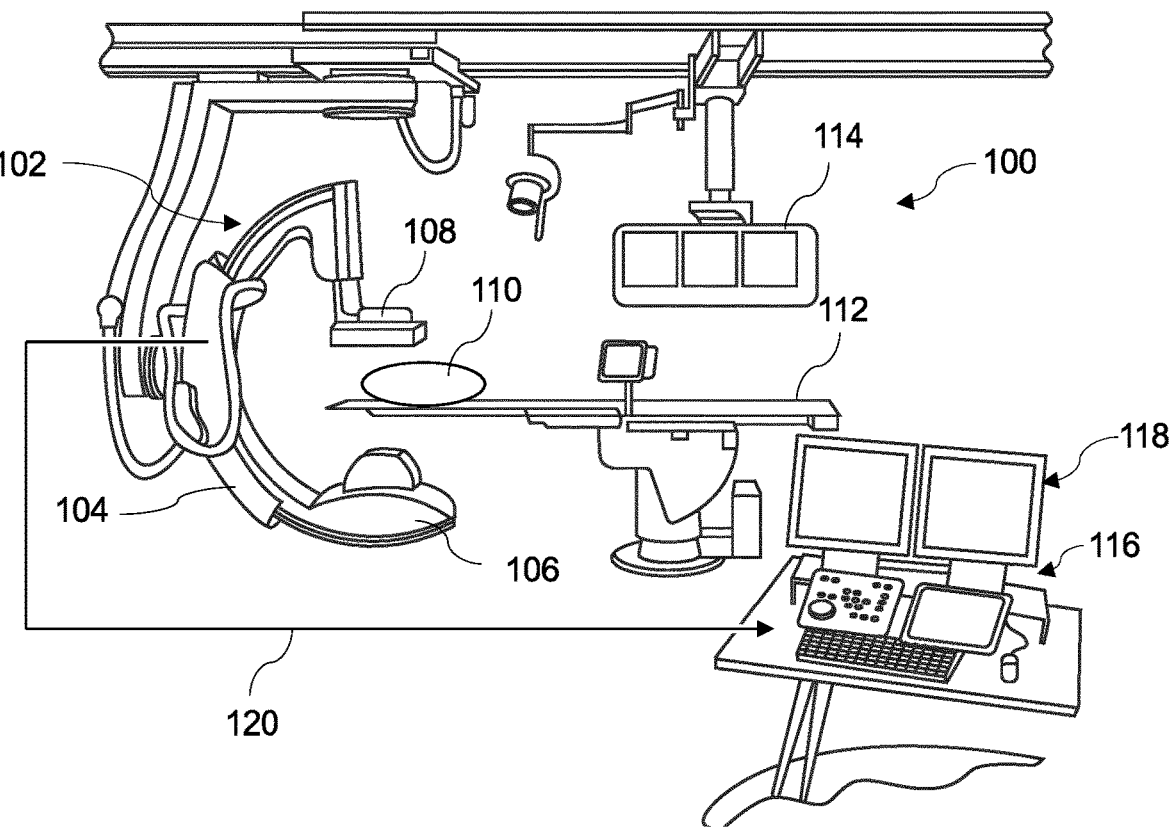
FIG. 2 schematically shows an example of a medical imaging system for assessment of vascular structures.

FIG. 2 schematically shows an example of a medical imaging system 100 for assessment of vascular structures. The system 100 comprises an X-ray imaging device 102 with an X-ray source and an X-ray detector. The system 100 further comprises an example of the device 10 for enhancing angiograms according to one of the preceding examples. The X-ray imaging device 102 is configured to provide the at least one angiographic image.

As an example, the X-ray imaging device 102 is shown as a ceiling mounted movable C-arm structure 104 with an X-ray source 106 and an X-ray detector 108 attached to ends of the C-arm. For illustration purposes, also an object 110, i.e. a subject, is shown supported by a patient support 112 for examination, intervention, other treatment or imaging purposes. The system 100 further comprises a display device 114, e.g. in form of a monitor arrangement shown movably suspended from a ceiling. The display device 114 is configured to display the at least one corrected angiogram. The system 100 also comprises an example 116 of the device 10 for enhancing angiograms according to one of the preceding and following examples. Further, again for illustration purposes, a control console with a monitor 118 and other user interface equipment like a mouse, a keyboard, a control panel and a touchpad is indicated on the right side. The device 116 for enhancing angiograms may be integrated in the control console. A line 120 indicates the data connection (wire or wireless) of the X-ray imaging device 102 and the device 116 for enhancing angiograms.

In an example, the data processor 14 is configured to select branches not of interest based on the identified possible branches and the determined branch of interest; and to estimate attenuation values of the selected branches not of interest.

In an example, for the subtraction, the data processor 14 is configured to:

i) subtract the complete estimated attenuation values of the branches not of interest from the angiographic image for the generation of the corrected angiogram: or ii) subtract a predetermined part of the respective estimated attenuation values from the angiographic image for the generation of the corrected angiogram.

In an example, for the determination of the angiographic image for identifying possible branches of the vascular structure, the data input 12 is configured to provide geometric image acquisition parameters comprising at least one of the group of direction and angulation. The data processor 14 is configured to, based on the geometric image acquisition parameters, select to be expected segments from a lookup table identifying possible segments that can be expected for certain geometric image acquisition parameters.

In another example, if no access to the angulation angles is available, those can be inferred by the images, e.g. via Deep Learning.

In a still further example, it is provided to learn (based on many examples, via DL) which branches in an image are of interest, without the proxy of the acquisition angles.

In another example, it is provided to rely on a pre-op CT to map the segmented maps to the CT branches, and understand which are well visible, i.e, not foreshortened, in the given view. Those would be the branches of interest.

In an example, the vascular structure of interest is the coronary artery tree. The lookup table is based on established clinical guidelines listing angiographic projections and optimal visualization of coronary artery segments (see FIG. 4).

In an example, the lookup table comprises different categories of preferences for the to be expected segments of the vascular structure. A change in the selection of the categories provides a change of the sensitivity of the determination of the angiographic image for identifying the possible branches of the vascular structure.

In an example, the data processor comprises a neural network configured to provide the semantic segmentation of the angiographic image for identifying the possible branches of the vascular structure by a deep learning procedure; and/or to provide the segmentation of the angiographic image for identifying the at least one branch of interest by a deep learning procedure.

It is noted that, from a technical point of view, segmentation refers to "binary segmentation": vessel/no vessel. However, semantic segmentation is a segmentation in different classes, i.e. "the group of pixels corresponding to the LAD branch" (→one given value on the segmentation map), "the group of pixels of the LCX branch" (→another given value in the segmentation map).

In an example, for the estimation of the attenuation values of the selected branches not of interest, the data processor 14 is configured to assume cylindrically shaped cross-sections for the branches.

In an example, the data processor 14 is configured to provide the estimation of the attenuation values of the selected branches not of interest for a plurality of locations along the respective selected branch. As an option, the data processor is configured to provide the estimation of the attenuation values for every pixel.

In an example, the data processor 14 is configured to combine the estimated attenuation values as attenuation profile. The data processor 14 is configured to:
  i) pre-process the attenuation profile comprising at least one the group of low pass filtering, bias correction or temporal background subtraction; and/or
  ii) post-process the attenuation profile comprising at least one of the group of sliding median filtering and robust spline fitting.

FIG. 3 shows basic steps of an example of a method 200 for enhancing angiograms. The method 200 comprising the following steps: In a first step 202, at least one angiographic image is provided showing a vascular structure of interest comprising a plurality of vessel branches. In a second step 204, at least one branch of interest from the angiographic is determined In a third step 206, the angiographic image is semantically segmented for identifying possible branches of the vascular structure. In a fourth step 208, branches based on the identified possible branches and the determined, i.e. identified, branch of interest are selected. In a fifth step 210, attenuation values of the selected branches are estimated. In a sixth step 212, at least a predetermined part of the estimated attenuation values is subtracted from the angiographic image generating a corrected angiogram. In a seventh step 214, the corrected angiogram is provided.

The vascular structure can also be referred to as vascular tree.

In an example, for the determining of the at least one branch of interest, it is provided segmenting the angiographic image for identifying at least one branch of interest.

In an example, more than one angiographic image is provided, for example a sequence of angiographic images.

The predetermined part can also be referred to as predetermined percentage, predetermined portion, predetermined fraction or predetermined ratio.

The segmenting of the angiographic image for identifying possible branches of the vascular structure can also be referred to as semantic segmentation.

The proposed solutions can be applied for stationary and mobile C-arm based X-ray systems.

In an example, this is independently applied frame by frame. In an option, some temporal consolidation is added that could improve the reliability of the steps. The angiogram correction is applied to coronary arteries but can be applied to any other vascular anatomy.

In an example, the corrected angiogram is shown to a user on a display.

In an example, it is provided:
  in the selecting of branches, branches not of interest are selected based on the identified possible branches and the identified branch of interest; and
  in the estimating of attenuation values, attenuation values of the selected branches not of interest are estimated.

In an example, it is provided:
  in the selecting of branches, branches of interest are selected based on the identified possible branches and the identified branch of interest; and
  in the estimating of attenuation values, attenuation values of the selected branches of interest are estimated.

In an example of the method, in the subtracting step, it is provided:

i) the complete estimated attenuation values are subtracted from the angiographic image for generating the corrected angiogram: or
  ii) a predetermined part of the respective estimated attenuation values is subtracted from the angiographic image for generating the corrected angiogram.

In the first option, the vessels that are not of interest are removed.

In the second option, the vessels that are not of interest could be attenuated instead of removed. As an example, 80% of the attenuation value that is estimated is removed. The output sequence would still show the further vessels, but the branch of interest would be emphasized. This helps in visualizing the vessel of interest, while keeping some anatomical information visible. This facilitates in reading the modified view, as the clinician intuitively understands that a part of the real vasculature (the removed vessels are still there) is shown. Additionally, this may visually make computation artefacts more acceptable. Instead of appearing over a relatively flat background, they would be part of attenuated yet still visible vessels, which may be visually less striking.

As a result, it is possible to remove the branches from an angiogram that were not meant to be analyzed from a certain view. In other words, it outputs a corrected angiogram that shows what would have been imaged if only the branch of interest had been present in the anatomy. Thus, an isolation of the branch of interest on an angiogram is achieved.

In an example, color-coding of the removed vessels is provided. For example, the complete attenuation, or nearly the complete attenuation, is removed and then some color, such as the blue color channel, is reinjected to a predetermined degree, such as 10%, 25% or even 50% or more.

If a certain imaging view is ideal to display the geometry of more than one branch, it is provided to generate several corrected angiograms, each one showing one (and only one) of these branches.

In an option, one angiogram is shown with several branches of interest.

In an example of the method, for segmenting the angiographic image for identifying possible branches of the vascular structure, geometric image acquisition parameters comprising at least one of the group of direction and angulation are provided, and, based on the geometric image acquisition parameters, to be expected segments are selected from a lookup table identifying possible segments that can be expected for certain geometric image acquisition parameters.

In an example of the method, the vascular structure of interest is the coronary artery tree; and the lookup table is based on established clinical guidelines listing angiographic projections and optimal visualization of coronary artery segments.

In an example of the method, the lookup table comprises different categories of preferences for the to be expected segments of the vascular structure. A change in the selection of the categories provides a change of the sensitivity of the segmenting of the angiographic image for identifying the possible branches of the vascular structure.

For example, for certain segments the lookup table provides categories like "view not recommended", "occasionally useful", "very useful" and "ideal view". By selecting only "ideal view" segments, a rather aggressive setting of the segmentation of possible segments would result.

In an example of the method, the segmenting of the angiographic image for identifying the possible branches of the vascular structure is guideline-based.

In an example of the method, the segmenting of the angiographic image for identifying the possible branches of the vascular structure is provided by a deep learning procedure. Alternatively, or in addition, the segmenting of the angiographic image for identifying the at least one branch of interest is provided by a deep learning procedure.

The deep learning procedure is provided by a neural network trained with numerous images showing a respective target segmentation provided manually by clinical experts.

In an example of the method, for the estimating of the attenuation values of the selected branches not of interest, cylindrically shaped cross-sections are assumed for the branches.

In an example of the method, the estimating of the attenuation values of the selected branches not of interest is provided all along the respective selected branch. In an option, the estimating of the attenuation values is provided for every pixel.

In another example of the method, the estimating of the attenuation values of the selected branches not of interest is provided for a plurality of locations along the respective selected branch and pixels in between are achieved by interpolation.

In an example of the method, the estimated attenuation values are combined as attenuation profile. In a first option, the attenuation profile is pre-processed comprising at least one the group of low pass filtering, bias correction or temporal subtraction (DSA). In a second option, in addition or alternatively, the attenuation profile is post-processed comprising at least one of the group of sliding median filtering and robust spline fitting.

FIG. 4 shows an example of a table 300 of related artery segments for certain viewing geometry 302. A marking 304 provides an indication for the respective suitability for the particular segment and the chosen geometry. FIG. 4 is from "Coronary angiography in the angioplasty era: projections with a meaning", C. di Mario, N. Sutaria, Heart, 91 (7): 968-976, July 2005. When having a certain imaging geometry, the information of the table can be used to select artery segments that are most likely visible in the image of the chosen geometry.

Figure 5:
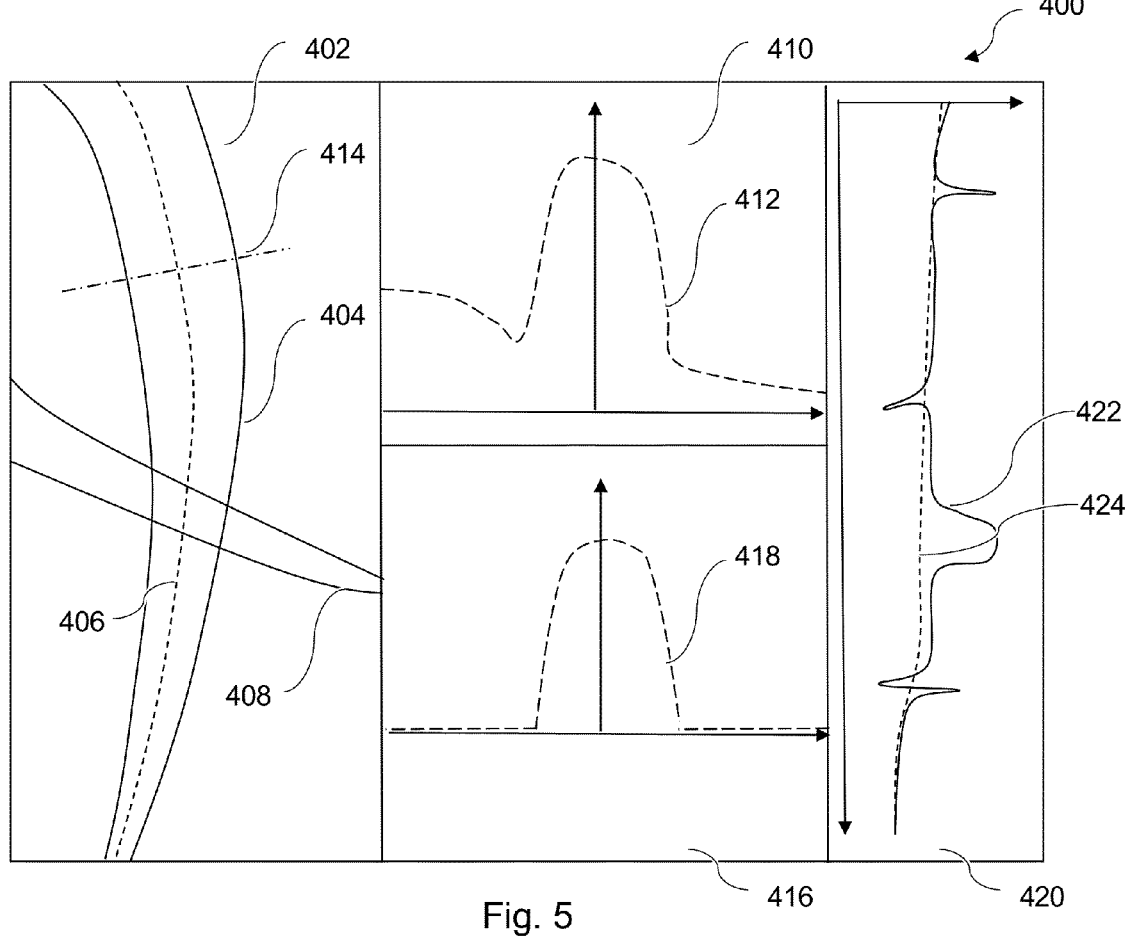
FIG. 5 shows an example of estimating attenuation values of vessels.

FIG. 5 shows an example of estimating attenuation values 400 of vessels. FIG. 5 illustrates the contrast attenuation estimation from a vessel segmentation and an angiogram. In FIG. 5 left part 402, a considered branch 404 is indicated with its centerline 406 shown in a hashed manner. The considered branch crosses another vessel 408. FIG. 5 center upper part 410, shows a profile 412 of the local contrast at one point of the centerline, for instance along the segment 414 in the left part. It exhibits a slowly decreasing shape due to the background low pass value. FIG. 5 center lower part 416 shows an ideal profile 418 of a locally cylindric vessel of the same radius. Estimating the amplitude of the profile is equivalent to estimating the local contrast of the vessel. FIG. 5 right part 420 shows an estimated attenuation (422, black) along the centerline and ideal attenuation (424, dotted line). A good estimate can be obtained by filtering the locally estimated values.

Figure 6:
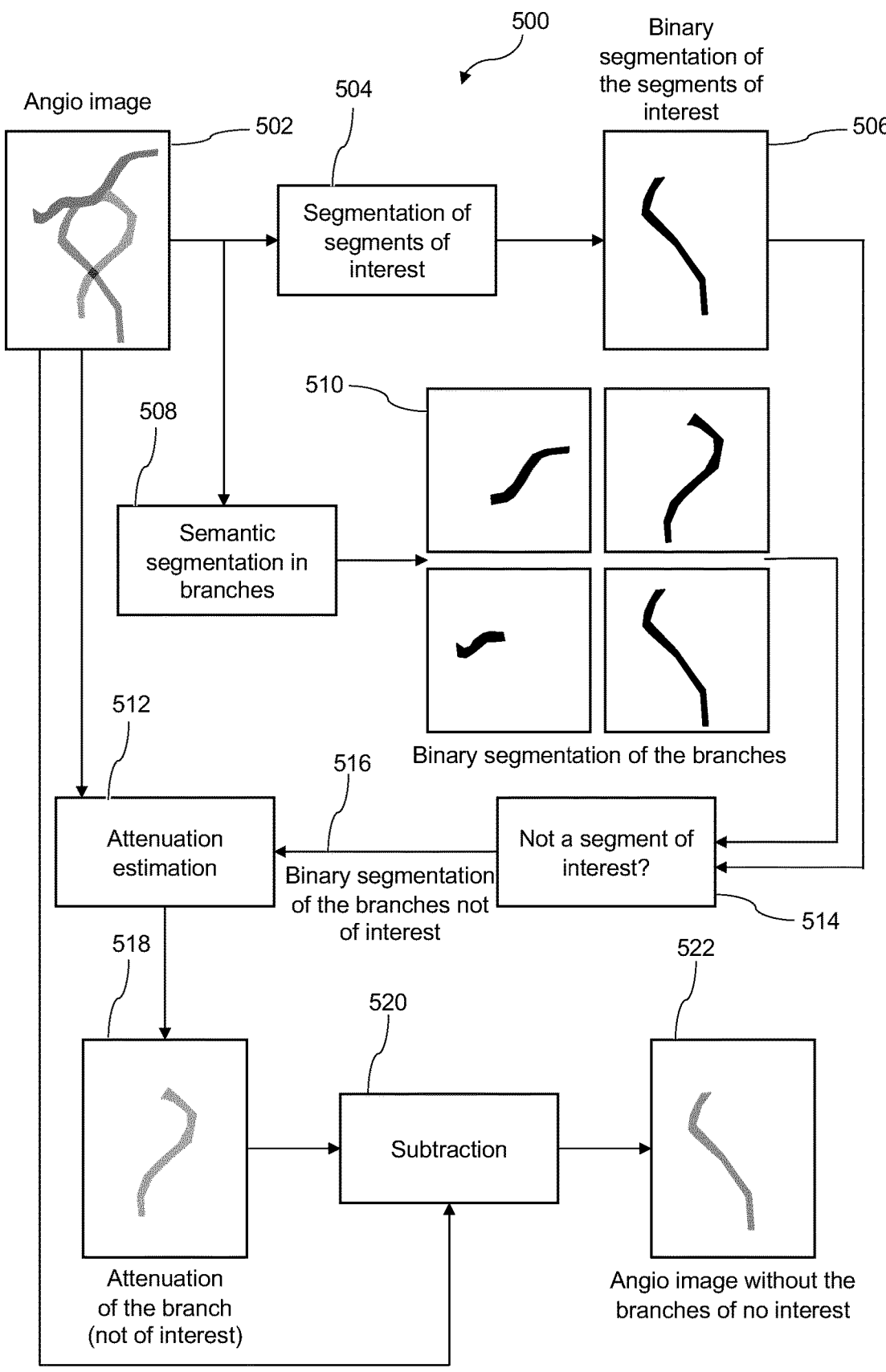
FIG. 6 shows a further example of a procedure to provide an enhanced angiogram.

FIG. 6 shows a further example of a procedure 500 to provide an enhanced angiogram. In a starting first frame, an angio image 502 is provided. The angio image 502 is then subject to a segmentation 504 of segments, e.g. segments of interest. The result is provided as binary segmentation 506 of the segments of interest. The angio image 502 is then subject to a semantic segmentation 508 in branches. The result is provided as binary segmentation 510 of the branches. As an important task, the attenuation is estimated 512. For this, the angio image 502 is provided. Further, also the binary segmentation 506 of the segments of interest are provided for an assessment if the segment is of interest, together with the binary segmentations 510 of the branches. The result is a binary segmentation of the branches not of interest 516, which is provided for the attenuation estimation 512. The latter produces an attenuation 518 of the branch (not of interest). The attenuation 518 is then used for a subtraction 520 generating an angio image 522 without the branches of no interest.

The term "subject" may also be referred to as individual. The "subject" may further also be referred to as patient, although it is noted that this term does not indicate whether any illness or disease is actually present with the subject.

In an example, a computer program or program element for controlling an apparatus according to one of the examples above is provided, which program or program element, when being executed by a processing unit, is adapted to perform the method steps of one of the method examples above.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for enhancing angiograms, the device comprising:

a processor configured to:

obtain at least one angiographic image showing a vascular structure of interest comprising a plurality of vessel branches;

determine at least one branch of interest from the angiographic image;

segment the angiographic image for identifying possible branches of the vascular structure;

select branches based on the identified possible branches and the determined branch of interest;

estimate attenuation values of the selected branches;

subtract at least a predetermined part of the estimated attenuation values from the angiographic image to generate a corrected angiogram; and provide the corrected angiogram.

2. The device according to claim 1, wherein the processor is further configured to:

select branches not of interest based on the identified possible branches and the determined branch of interest; and estimate attenuation values of the selected branches not of interest.

3. The device according to claim 2, wherein, for the subtraction, the data-processor is further configured to:

subtract the complete estimated attenuation values of the branches not of interest from the angiographic image for the generation of the corrected angiogram; or subtract a predetermined part of the respective estimated attenuation values from the angiographic image for the generation of the corrected angiogram.

4. The device according to claim 2, wherein, for the estimation of the attenuation values of the selected branches not of interest, the processor is further configured to assume cylindrically shaped cross-sections for the branches.

5. The device according to claim 1, wherein, for the segmentation of the angiographic image for identifying possible branches of the vascular structure, the processor is further configured to:

obtain geometric image acquisition parameters comprising at least one of direction and angulation; and based on the geometric image acquisition parameters, select expected segments from a lookup table identifying possible segments expected for one or more of the geometric image acquisition parameters.

6. The device according to claim 5, wherein the vascular structure of interest is a coronary artery tree; and wherein the lookup table is based on established guidelines listing angiographic projections and optimal visualization of coronary artery segments.

7. The device according to claim 5, wherein the lookup table comprises different categories of preferences for the to be expected segments of the vascular structure; and wherein a change in the selection of the categories provides a change of the sensitivity of the segmenting of the angiographic image for identifying the possible branches of the vascular structure.

8. The device according to claim 1, wherein the processor is configured to apply a neural network configured to at least one of:

provide semantic segmentation of the angiographic image for identifying the possible branches of the vascular structure by a deep learning procedure; and provide the semantic segmentation of the angiographic image for identifying the at least one branch of interest by a deep learning procedure.

9. The device according to claim 1, wherein the processor is further configured to:

combine the estimated attenuation values as attenuation profile; and at least one of:

i) pre-process the attenuation profile comprising at least one of low pass filtering, bias correction, and temporal subtraction; and ii) post-process the attenuation profile comprising at least one of sliding median filtering and robust spline fitting.

10. The device according to claim 1, further comprising a display configured to display the corrected angiogram.

11. A medical imaging system for assessment of vascular structures, the system comprising:

an X-ray imaging device with an X-ray source and an X-ray detector; and the device for enhancing angiograms according to claim 1;

wherein the X-ray imaging device is configured to provide the at least one angiographic image.

12. A method for enhancing angiograms, the method comprising:

providing at least one angiographic image showing a vascular structure of interest comprising a plurality of vessel branches;

determining at least one branch of interest from the angiographic image;

segmenting the angiographic image for identifying possible branches of the vascular structure;

selecting branches based on the identified possible branches and the determined branch of interest;

estimating attenuation values of the selected branches;

subtracting at least a predetermined part of the estimated attenuation values from the angiographic image generating a corrected angiogram; and providing the corrected angiogram.

13. The method according to claim 12, wherein:

in the selecting of branches, branches not of interest are selected based on the identified possible branches and the determined branch of interest; and in the estimating of attenuation values, attenuation values of the selected branches not of interest are estimated.

14. The method according to claim 12, wherein the subtracting further comprises:

subtracting the complete estimated attenuation values of branches not of interest from the angiographic image for the generation of the corrected angiogram; or subtracting a predetermined part of the respective estimated attenuation values from the angiographic image for the generation of the corrected angiogram.

15. The method according to claim 12, wherein the segmenting of the angiographic image for identifying possible branches of the vascular structure further comprises:

obtaining geometric image acquisition parameters comprising at least one of direction and angulation; and based on the geometric image acquisition parameters, selecting expected segments from a lookup table identifying possible segments expected for one or more of the geometric image acquisition parameters.

16. The method according to claim 12, further comprising applying a neural network for at least one of:

providing semantic segmentation of the angiographic image for identifying the possible branches of the vascular structure by a deep learning procedure; and providing the semantic segmentation of the angiographic image for identifying the at least one branch of interest by the deep learning procedure.

17. A non-transitory computer-readable storage medium having stored instructions which, when executed by a processor, cause the processor to:

obtain at least one angiographic image showing a vascular structure of interest comprising a plurality of vessel branches;

determine at least one branch of interest from the angiographic image; segment the angiographic image for identifying possible branches of the vascular structure;

select branches based on the identified possible branches and the determined branch of interest;

estimate attenuation values of the selected branches;

subtract at least a predetermined part of the estimated attenuation values from the angiographic image to generate a corrected angiogram; and provide the corrected angiogram.

18. The non-transitory computer-readable storage medium of claim 17, wherein the instructions, when executed by a processor, further cause the processor to, for the subtraction:

subtract the complete estimated attenuation values of branches not of interest from the angiographic image for the generation of the corrected angiogram; or subtract a predetermined part of the respective estimated attenuation values from the angiographic image for the generation of the corrected angiogram.

19. The non-transitory computer-readable storage medium of claim 17, wherein the instructions, when executed by a processor, further cause the processor to:

obtain geometric image acquisition parameters comprising at least one of direction and angulation; and based on the geometric image acquisition parameters, select expected segments from a lookup table identifying possible segments expected for one or more of the geometric image acquisition parameters.

20. The non-transitory computer-readable storage medium of claim 17, wherein the instructions, when executed by a processor, further cause the processor to apply a neural network configured to at least one of:

provide semantic segmentation of the angiographic image for identifying the possible branches of the vascular structure by a deep learning procedure; and provide the semantic segmentation of the angiographic image for identifying the at least one branch of interest by the deep learning procedure.

* * * * *